(12) United States Patent
Gentile et al.

(10) Patent No.: US 7,928,108 B2
(45) Date of Patent: Apr. 19, 2011

(54) PYRIDINONE DERIVATIVE FOR THE TREATMENT OF PREMATURE EJACULATION

(75) Inventors: Gabriella Gentile, Verona (IT); Valeria Zucchelli, Verona (IT)

(73) Assignee: Glaxo Group Limited, Greenford, Middlesex (GB)

( * ) Notice: Subject to any disclaimer, the term of this patent is extended or adjusted under 35 U.S.C. 154(b) by 0 days.

(21) Appl. No.: 12/594,386

(22) PCT Filed: Apr. 3, 2008

(86) PCT No.: PCT/EP2008/053978
§ 371 (c)(1),
(2), (4) Date: Oct. 2, 2009

(87) PCT Pub. No.: WO2008/122561
PCT Pub. Date: Oct. 16, 2008

(65) Prior Publication Data
US 2010/0075982 A1    Mar. 25, 2010

(30) Foreign Application Priority Data
Apr. 5, 2007  (GB) .................................. 0706772.1

(51) Int. Cl.
*A61K 31/4709* (2006.01)
*C07D 401/12* (2006.01)
(52) U.S. Cl. .................................. 514/253.07; 544/363
(58) Field of Classification Search .................. None
See application file for complete search history.

(56) References Cited

FOREIGN PATENT DOCUMENTS
WO  WO 2004/046124 A    6/2004

OTHER PUBLICATIONS

Waldinger et al. Expert Opin.Emerging Drugs, vol. 11(1): 99-109 (2006).*

* cited by examiner

*Primary Examiner* — Emily Bernhardt
(74) *Attorney, Agent, or Firm* — Duke M. Fitch; Kathryn L. Sieburth; John Lemanowicz

(57) ABSTRACT

The invention provides 3-(methyloxy)-1-{4-[4-(2-methyl-5-quinolinyl)-1-piperazinyl]butyl}-2(1H)-pyridinone of formula (I),

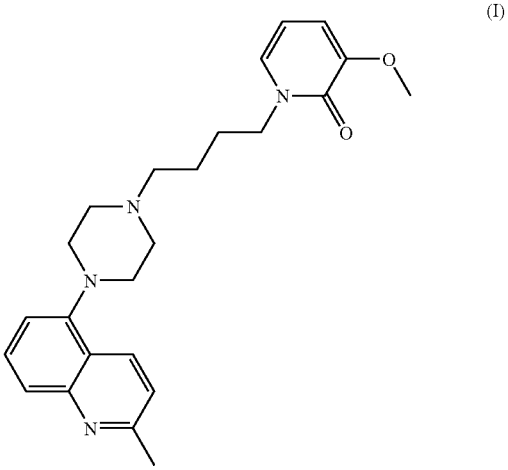

or a pharmaceutically acceptable salt thereof.

4 Claims, No Drawings

PYRIDINONE DERIVATIVE FOR THE TREATMENT OF PREMATURE EJACULATION

This application is a 371 of International Application No. PCT/EP2008/053978, filed 3 Apr. 2008, which claims the priority of GB Application No. 0706772.1, filed 5 Apr. 2007.

This invention relates to a novel pyridinone derivative. The invention also relates to the use of the derivative in treating diseases and conditions mediated by antagonism of the 5-$HT_{1A}$ receptor, in particular premature ejaculation. In addition, the invention relates to compositions containing the derivative and processes for its preparation.

According to a first aspect, the invention provides 3-(methyloxy)-1-{4-[4-(2-methyl-5-quinolinyl)-1-piperazinyl]butyl}-2(1H)-pyridinone of formula (I),

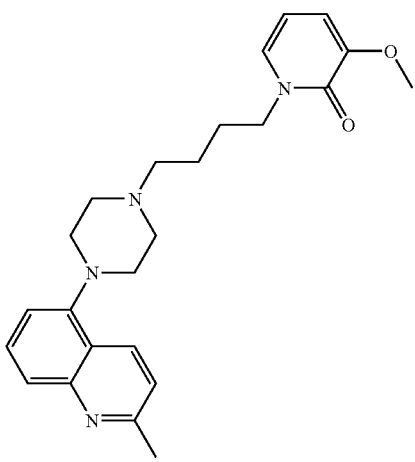

(I)

or a pharmaceutically acceptable salt thereof.

The compound of formula (I) may form pharmaceutically or veterinarily acceptable salts, for example, non-toxic acid addition salts formed with inorganic acids such as hydrochloric, hydrobromic, hydroiodic, sulfuric and phosphoric acid, with carboxylic acids or with organo-sulfonic acids. Examples include the HCl, HBr, HI, sulfate or bisulfate, nitrate, phosphate or hydrogen phosphate, acetate, benzoate, succinate, saccharate, fumarate, maleate, lactate, citrate, tartrate, gluconate, camsylate, methanesulfonate, ethanesulfonate, benzenesulfonate, p-toluenesulfonate and pamoate salts. For reviews on suitable pharmaceutical salts see Berge et al, J. Pharm, Sci., 66, 1-19, 1977; P L Gould, International Journal of Pharmaceutics, 33 (1986), 201-217; and Bighley et al, Encyclopedia of Pharmaceutical Technology, Marcel Dekker Inc, New York 1996, Volume 13, page 453-497.

Hereinafter, the compound of formula (I) and its pharmaceutically acceptable salts, are referred to as "the compounds of the invention".

It will be appreciated by those skilled in the art that certain protected derivatives of the compounds of the invention, which may be made prior to a final deprotection stage, may not possess pharmacological activity as such, but may, in certain instances, be administered orally or parenterally and thereafter metabolised in the body to form compounds defined in the first aspect which are pharmacologically active. Such derivatives may therefore be described as "prodrugs". All protected derivatives and prodrugs of compounds defined in the first aspect are included within the scope of the invention. Examples of suitable pro-drugs for the compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1 (the disclosures in which documents are incorporated herein by reference). It will further be appreciated by those skilled in the art, that certain moieties, known to those skilled in the art as "promoieties", for example as described by H. Bundgaard in "Design of Prodrugs" (the disclosure in which document is incorporated herein by reference) may be placed on appropriate functionalities when such functionalities are present within the compound defined in the first aspect.

The compounds of the invention may exist in solvated or hydrated form.

The compounds of the invention or solvates/hydrates of the compounds or salts, may exist in one or more polymorphic form.

Therefore, the invention provides a solvate or prodrug of the compounds of the invention.

The compounds of the invention may exist in one or more tautomeric forms. All tautomers and mixtures thereof are included in the scope of the present invention. For example, a claim to 2-hydroxypyridyl would also cover its tautomeric form, α-pyridinonyl.

The invention also includes all suitable isotopic variations of the compounds of the invention. An isotopic variation is defined as one in which at least one atom is replaced by an atom having the same atomic number but an atomic mass different from the atomic mass usually found in nature. Examples of isotopes that can be incorporated include isotopes of hydrogen, carbon, nitrogen and oxygen such as $^2H$, $^3H$, $^{13}C$, $^{14}C$, $^{15}N$, $^{17}O$ and $^{18}O$ respectively. Certain isotopic variations, for example, those in which a radioactive isotope such as $^3H$ or $^{14}C$ is incorporated, are useful in drug and/or substrate tissue distribution studies. Tritiated, i.e. $^3H$, and carbon-14, i.e. $^{14}C$, isotopes are suitable for their ease of preparation and detectability. Further, substitution with isotopes such as deuterium, i.e. $^2H$, may afford certain therapeutic advantages resulting from greater metabolic stability, for example, increased in vivo half-life or reduced dosage requirements and hence may be suitable in some circumstances. Isotopic variations can generally be prepared by conventional procedures such as by the illustrative methods or by the preparations described in the Examples and Descriptions hereafter using appropriate isotopic variations of suitable reagents.

The compounds of the invention are effective antagonists of the 5-$HT_{1A}$ receptor. In addition, the compounds of the invention have high selectivity for the 5-$HT_{1A}$ receptor over the 5-$HT_{1B}$ receptor, i.e. the compounds are better antagonists of the 5-$HT_{1A}$ receptor than they are antagonists of the 5-$HT_{1B}$ receptor.

It is believed that the compounds of the invention are useful for the treatment of diseases and conditions mediated by antagonism of the 5-$HT_{1A}$ receptor.

Therefore, according to a further aspect, the invention provides the compounds of the invention for use in therapy, preferably a human therapy.

According to a further aspect, the invention provides the use of the compounds of the invention in the manufacture of a medicament for treating sexual dysfunction.

In an embodiment the sexual dysfunction is selected from the list consisting of: Sexual Desire Disorders (including Hypoactive Sexual Desire Disorder (302.71) and Sexual Aversion Disorder (302.79)); sexual arousal disorders (including Female Sexual Arousal Disorder (302.72) and Male Erectile Disorder (302.72)); orgasmic disorders (including Female Orgasmic Disorder (302.73), Male Orgasmic Disorder (302.74) and Premature Ejaculation (302.75)); sexual pain disorder (including Dyspareunia (302.76) and Vaginismus (306.51)); Sexual Dysfunction Not Otherwise Specified (302.70); paraphilias (including Exhibitionism (302.4), Fetishism (302.81), Frotteurism (302.89), Pedophilia (302.2), Sexual Masochism (302.83), Sexual Sadism (302.84), Transvestic Fetishism (302.3), Voyeurism (302.82) and Paraphilia Not Otherwise Specified (302.9)); gender identity disorders (including Gender Identity Disorder in Children (302.6) and Gender Identity Disorder in Adolescents or Adults (302.85)); and Sexual Disorder Not Otherwise Specified (302.9).

In a further embodiment, the sexual dysfunction is premature ejaculation.

The compounds of the invention may also treat diseases or conditions selected from the list consisting of: [the numbers in brackets after the listed diseases below refer to the classification code in Diagnostic and Statistical Manual of Mental Disorders, 4th Edition, published by the American Psychiatric Association (DSM-IV) and/or the International Classification of Diseases, 10th Edition (ICD-10)]:

i) Psychotic disorders for example Schizophrenia (including the subtypes Paranoid Type (295.30), Disorganised Type (295.10), Catatonic Type (295.20), Undifferentiated Type (295.90) and Residual Type (295.60)); Schizophreniform Disorder (295.40); Schizoaffective Disorder (295.70) (including the subtypes Bipolar Type and Depressive Type); Delusional Disorder (297.1) (including the subtypes Erotomanic Type, Grandiose Type, Jealous Type, Persecutory Type, Somatic Type, Mixed Type and Unspecified Type); Brief Psychotic Disorder (298.8); Shared Psychotic Disorder (297.3); Psychotic Disorder due to a General Medical Condition (including the subtypes with Delusions and with Hallucinations); Substance-Induced Psychotic Disorder (including the subtypes with Delusions (293.81) and with Hallucinations (293.82)); and Psychotic Disorder Not Otherwise Specified (298.9).

ii) Depression and mood disorders for example Depressive Episodes (including Major Depressive Episode, Manic Episode, Mixed Episode and Hypomanic Episode); Depressive Disorders (including Major Depressive Disorder, Dysthymic Disorder (300.4), Depressive Disorder Not Otherwise Specified (311)); Bipolar Disorders (including Bipolar I Disorder, Bipolar II Disorder (i.e. Recurrent Major Depressive Episodes with Hypomanic Episodes) (296.89), Cyclothymic Disorder (301.13) and Bipolar Disorder Not Otherwise Specified (296.80)); Other Mood Disorders (including Mood Disorder due to a General Medical Condition (293.83) which includes the subtypes With Depressive Features, With Major Depressive-like Episode, With Manic Features and With Mixed Features); Substance-Induced Mood Disorder (including the subtypes With Depressive Features, With Manic Features and With Mixed Features); and Mood Disorder Not Otherwise Specified (296.90).

iii) Anxiety disorders for example Social Anxiety Disorder; Panic Attack; Agoraphobia, Panic Disorder; Agoraphobia Without History of Panic Disorder (300.22); Specific Phobia (300.29) (including the subtypes Animal Type, Natural Environment Type, Blood-Injection-Injury Type, Situational Type and Other Type); Social Phobia (300.23); Obsessive-Compulsive Disorder (300.3); Posttraumatic Stress Disorder (309.81); Acute Stress Disorder (308.3); Generalized Anxiety Disorder (300.02); Anxiety Disorder Due to a General Medical Condition (293.84); Substance-Induced Anxiety Disorder; and Anxiety Disorder Not Otherwise Specified (300.00).

iv) Substance-related disorders for example Substance Use Disorders (including Substance Dependence, Substance Craving and Substance Abuse); Substance-Induced Disorders (including Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders (including Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9)); Amphetamine (or Amphetamine-Like)-Related Disorders (for example Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9)); Caffeine Related Disorders (including Caffeine Intoxication (305.90), Caffeine-Induced Anxiety Disorder, Caffeine-Induced Sleep Disorder and Caffeine-Related Disorder Not Otherwise Specified (292.9)); Cannabis-Related Disorders (including Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9)); Cocaine-Related Disorders (including Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9)); Hallucinogen-Related Disorders (including Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9)); Inhalant-Related Disorders (including Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9)); Nicotine-Related Disorders (including Nicotine Dependence (305.1), Nicotine Withdrawal (292.0) and Nicotine-Related Disorder Not Otherwise Specified (292.9)); Opioid-Related Disorders (including Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9)); Phencyclidine (or Phencyclidine-Like)-Related Disorders (including Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9)); Sedative-, Hypnotic-, or Anxiolytic-Related Disorders (including Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9)); Polysubstance-Related Disorder (including Polysubstance Dependence (304.80)); and Other (or Unknown) Substance-Related Disorders (including Anabolic Steroids, Nitrate Inhalants and Nitrous Oxide).

v) Sleep disorders for example primary sleep disorders such as Dyssomnias (including Primary Insomnia (307.42), Primary Hypersomnia (307.44), Narcolepsy (347), Breathing-Related Sleep Disorders (780.59), Circadian Rhythm Sleep Disorder (307.45) and Dyssomnia Not Otherwise Specified (307.47)); primary sleep disorders such as Parasomnias (including Nightmare Disorder (307.47), Sleep Terror Disorder (307.46), Sleepwalking Disorder (307.46) and Parasomnia Not Otherwise Specified (307.47)); Sleep Disorders Related to Another Mental Disorder (including Insomnia Related to Another Mental Disorder (307.42) and Hypersomnia Related to Another Mental Disorder (307.44)); Sleep Disorder Due to a General Medical Condition; and Substance-Induced Sleep Disorder (including the subtypes Insomnia Type, Hypersomnia Type, Parasomnia Type and Mixed Type).

vi) Eating disorders such as Anorexia Nervosa (307.1) (including the subtypes Restricting Type and Binge-Eating/Purging Type); Bulimia Nervosa (307.51) (including the subtypes Purging Type and Nonpurging Type); Obesity; Compulsive Eating Disorder; Binge Eating Disorder; and Eating Disorder Not Otherwise Specified (307.50).

vii) Autism Spectrum Disorders including Autistic Disorder (299.00), Asperger's Disorder, Rett's Disorder, Childhood Disintegrative Disorder and Pervasive Developmental Disorder Not Otherwise Specified.

viii) Attention-Deficit/Hyperactivity Disorder (including the subtypes Attention-Deficit/Hyperactivity Disorder Combined Type (314.01), Attention-Deficit/Hyperactivity Disorder Predominantly Inattentive Type (314.00), Attention-Deficit/Hyperactivity Disorder Hyperactive-Impulse Type (314.01) and Attention-Deficit/Hyperactivity Disorder Not Otherwise Specified (314.9)); Hyperkinetic Disorder; Disruptive Behaviour Disorders such as Conduct Disorder (including the subtypes childhood-onset type (321.81), Adolescent-Onset Type (312.82) and Unspecified Onset (312.89), Oppositional Defiant Disorder (313.81) and Disruptive Behaviour Disorder Not Otherwise Specified; and Tic Disorders such as Tourette's Disorder (307.23).

ix) Personality Disorders including the subtypes Paranoid Personality Disorder (301.0), Schizoid Personality Disorder (301.20), Schizotypal Personality Disorder (301.22), Antisocial Personality Disorder (301.7), Borderline Personality Disorder (301.83), Histrionic Personality Disorder (301.50), Narcissistic Personality Disorder (301.81), Avoidant Personality Disorder (301.82), Dependent Personality Disorder (301.6), Obsessive-Compulsive Personality Disorder (301.4) and Personality Disorder Not Otherwise Specified (301.9).

x) Enhancement of cognition including the treatment of cognition impairment in other diseases such as schizophrenia, bipolar disorder, depression, other psychiatric disorders and psychotic conditions associated with cognitive impairment, e.g. Alzheimer's disease.

It will be appreciated that references herein to "treatment" extend to prophylaxis, prevention of recurrence and suppression or amelioration of symptoms (whether mild, moderate or severe) as well as the treatment of established conditions. The compound of the invention may be administered as the raw chemical but the active ingredient is suitably presented as a pharmaceutical formulation.

The compounds of the invention may be used in combination with the following agents to treat or prevent psychotic disorders: i) antipsychotics; ii) drugs for extrapyramidal side effects, for example anticholinergics (such as benztropine, biperiden, procyclidine and trihexyphenidyl), antihistamines (such as diphenhydramine) and dopaminergics (such as amantadine); iii) antidepressants; iv) anxiolytics; and v) cognitive enhancers for example cholinesterase inhibitors (such as tacrine, donepezil, rivastigmine and galantamine).

The compounds of the invention may be used in combination with antidepressants to treat or prevent depression and mood disorders.

The compounds of the invention may be used in combination with the following agents to treat or prevent bipolar disease: i) mood stabilisers; ii) antipsychotics; and iii) antidepressants.

The compounds of the invention may be used in combination with the following agents to treat or prevent anxiety disorders: i) anxiolytics; and ii) antidepressants.

The compounds of the invention may be used in combination with the following agents to treat or prevent male sexual dysfunction: i) phosphodiesterase V inhibitors, for example vardenafil and sildenafil; ii)) dopamine agonists/dopamine antagonists/dopamine transport inhibitors for example apomorphine and buproprion; iii) alpha adrenoceptor antagonists for example phentolamine; iv) prostaglandin agonists for example alprostadil; v) androgen receptor modulators such as testosterone; vi) serotonin agonists/antagonists/modulators/serotonin transporter inhibitors for example serotonin reuptake inhibitors; vii) noradrenaline transport inhibitors for example reboxetine; viii) oxytocin receptor antagonists; (ix) sodium and calcium channel inhibitors/blockers; and (x) opioid receptor antagonists.

The compounds of the invention may be used in combination with the same agents specified for male sexual dysfunction to treat or prevent female sexual dysfunction, and in addition an estrogen agonist such as estradiol.

Antipsychotic drugs include Typical Antipsychotics (for example chlorpromazine, thioridazine, mesoridazine, fluphenazine, perphenazine, prochlorperazine, trifluoperazine, thiothixine, haloperidol, molindone and loxapine); and Atypical Antipsychotics (for example clozapine, olanzapine, risperidone, quetiapine, aripirazole, ziprasidone and amisulpride).

Antidepressant drugs include serotonin reuptake inhibitors (such as citalopram, escitalopram, fluoxetine, paroxetine, sertraline femoxetine, fluvoxamine, indalpine and zimeldine); dual serotonin/noradrenaline reuptake inhibitors (such as venlafaxine, duloxetine and milnacipran); Noradrenaline reuptake inhibitors (such as reboxetine and venlafaxine); tricyclic antidepressants (such as amitriptyline, clomipramine, imipramine, maprotiline, nortriptyline and trimipramine); monoamine oxidase inhibitors (such as isocarboxazide, moclobemide, phenelzine and tranylcypromine); and others (such as bupropion, mianserin, mirtazapine, nefazodone and trazodone).

Mood stabiliser drugs include lithium, sodium valproate/valproic acid/divalproex, carbamazepine, lamotrigine, gabapentin, topiramate and tiagabine.

Anxiolytics include benzodiazepines such as alprazolam and lorazepam.

In addition the compounds of the invention may be administered in combination with 5-HT$_3$ antagonists (such as ondansetron, granisetron and metoclopramide); serotonin agonists (such as sumatriptan, rauwolscine, yohimbine and metoclopramide); and NK-1 antagonists.

It will be appreciated that the compound of the combination or composition may be administered simultaneously (either in the same or different pharmaceutical formulations), separately or sequentially.

The compounds of the invention will normally, but not necessarily, be formulated into pharmaceutical compositions prior to administration to a patient by an appropriate route. Accordingly, in a further aspect, the invention provides pharmaceutical compositions comprising a compound of the invention and one or more pharmaceutically-acceptable excipients.

As used herein, "pharmaceutically-acceptable excipient" means any pharmaceutically acceptable material present in the pharmaceutical composition or dosage form other than the compound or compounds of the invention. Typically the material gives form, consistency and performance to the pharmaceutical composition.

The pharmaceutical compositions of the invention typically contain one compound of the invention. However, in certain embodiments, the pharmaceutical compositions of the invention contain more than one compound of the invention. In addition, the pharmaceutical compositions of the invention may comprise one or more additional pharmaceutically active compounds.

Such pharmaceutical compositions of the invention may be prepared and packaged in bulk form wherein a safe and effective amount of a compound of the invention can be dispensed and then given to the patient such as with powders or syrups. Alternatively, the pharmaceutical compositions of the invention may be prepared and packaged as dosage forms wherein each physically discrete dosage form contains a safe and effective amount of a compound of the invention. Accordingly, in another aspect, the invention provides dosage forms comprising pharmaceutical compositions of the invention. Each discrete dosage form contains from 1 mg to 500 mg of a compound of the invention. In another aspect, each discrete dosage form contains from 5 mg to 400 mg of a compound of the invention. In another aspect, each discrete dosage form contains from 10 mg to 300 mg of a compound of the invention. In another aspect, each discrete dosage form contains from 20 mg to 300 mg of a compound of the invention.

It will be recognised by one of skill in the art that the optimal quantity and spacing of individual dosages of compounds of the invention will be determined by the nature and extent of the condition being treated, the form, route and site of administration, and the particular mammal being treated, and that such optimums can be determined by conventional techniques. It will also be appreciated by one of skill in the art that the optimal course of treatment, i.e. the number of doses of compounds of the invention given per day for a defined number of days, can be ascertained by those skilled in the art using conventional course of treatment determination tests.

The compositions of the invention will typically be formulated into dosage forms which are adapted for administration to the patient by the desired route of administration. For example, dosage forms include those adapted for (1) oral administration such as tablets, capsules, caplets, pills, lozenges, powders, syrups, elixirs, suspensions, solutions, emulsions, sachets and cachets; (2) parenteral administration such as sterile solutions, suspensions, implants and powders for reconstitution; (3) transdermal administration such as transdermal patches; (4) rectal and vaginal administration such as suppositories, pessaries and foams; (5) inhalation and intranasal such as dry powders, aerosols, suspensions and solutions (sprays and drops); (6) topical administration such as creams, ointments, lotions, solutions, pastes, drops, sprays, foams and gels; (7) ocular administration such as drops, ointment, sprays, suspensions and inserts; (8) buccal and sublingual administration such as lozenges, patches, sprays, drops, chewing gums and tablets.

Suitable pharmaceutically-acceptable excipients will vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting of the compound or compounds of the invention once administered to the patient from one organ, or portion of the body, to another organ, or portion of the body. Certain pharmaceutically-acceptable excipients may be chosen for their ability to enhance patient compliance. Certain pharmaceutically-acceptable excipients may be chosen for their ability to facilitate the release of the compound of the invention at the appropriate rate to treat the condition.

Suitable pharmaceutically-acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavouring agents, flavour masking agents, colouring agents, anticaking agents, humectants, chelating agents, plasticizers, viscosity increasing agents, rate modifying agents, antioxidants, preservatives, stabilizers, surfactants and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to determine suitable pharmaceutically-acceptable excipients in appropriate amounts for use with the compounds of the invention. In addition, there are a number of resources that are available to the skilled artisan which describe pharmaceutically-acceptable excipients and may be useful in selecting suitable pharmaceutically-acceptable excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press). The pharmaceutical compositions of the invention may be prepared using techniques and methods known to those skilled in the art. Some of the methods commonly used in the art are described in Remington's Pharmaceutical Sciences (Mack Publishing Company).

In one aspect, the invention is directed to a solid oral dosage form such as a tablet or capsule comprising a safe and effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch and pre-gelatinized starch), gelatin, acacia, sodium alginate, alginic acid, tragacanth, guar gum, povidone, and cellulose and its derivatives (e.g. hydroxypropyl methyl cellulose). The oral solid dosage form may further comprise a disintegrant. Suitable disintegrants include starches, crospovidone, sodium starch glycolate, cros-carmellose, alginic acid, and sodium carboxymethyl cellulose. The oral solid dosage form may further comprise a lubricant. Suitable lubricants include stearic acid, magnesium stearate, calcium stearate, and sodium dodecyl sulphate. The oral solid dosage form may further comprise a glidant such as talc and colloidal silicon dioxide. The oral solid dosage form may further comprise an outer coating which may have cosmetic or functional properties.

All publications, including, but not limited to, patents and patent applications cited in this specification, are herein incorporated by reference as if each individual publication were specifically and individually indicated to be incorporated by reference herein as though fully set forth.

It will be appreciated that the invention includes the following further aspects. The diseases and conditions described above extend, where appropriate, to these further aspects.
 i) The compounds of the invention for use in treating sexual dysfunction, such as premature ejaculation.
 ii) A method of treatment of sexual dysfunction (such as premature ejaculation) in a mammal comprising administering an effective amount of the compounds of the invention.

3-(Methyloxy)-1-{-4-[4-(2-methyl-5-quinolinyl)-1-piperazinyl]butyl}-2(1H)-pyridinone hydrochloride may be prepared as follows.

1-(4-Chlorobutyl)-3-(methyloxy)-2(1H)-pyridinone

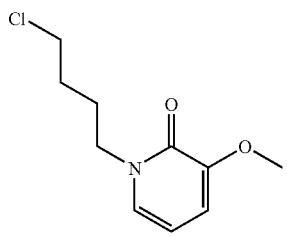

A mixture of 3-methoxy-2(1H)-pyridone (0.54 g, 4.31 mmol) and potassium carbonate (0.71 g, 5.14 mmol) in anhydrous N,N-dimethylformamide (20 mL) was stirred at room temperature for 1 h. 1-Bromo-4-chlorobutane (0.50 mL, 4.33 mmol) was then added and the resulting reaction mixture was stirred at room temperature overnight. The reaction mixture was quenched with water (20 mL) and extracted with dichloromethane (3×30 mL). The organic layers were collected, dried over $Na_2SO_4$ and concentrated in vacuo. The crude product was purified by flash chromatography on silica gel, eluting with 100% dichloromethane and 5% methanol in dichloromethane to afford the title compound as a pale yellow oil (0.39 g, 42%). $^1$H NMR (400 MHz, $CDCl_3$) δ ppm 6.87 (dd, 1H) 6.59 (dd, 1H) 6.10 (t, 1H) 4.02 (t, 2H) 3.81 (s, 3H) 3.57 (t, 2H) 2.01-1.87 (m, 2H) 1.87-1.73 (m, 2H).

3-(Methyloxy)-1-{4-[4-(2-methyl-5-quinolinyl)-1-piperazinyl]butyl}-2(1H)-pyridinone hydrochloride

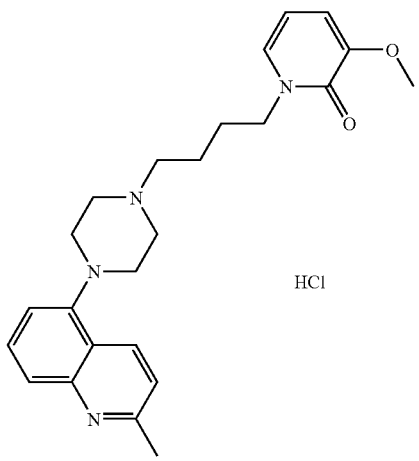

A mixture of 1-(4-chlorobutyl)-3-(methyloxy)-2(1H)-pyridinone (67.8 mg, 0.31 mmol), 2-methyl-5-(1-piperazinyl)quinoline (see WO2004/046124 D3) (77.5 mg, 0.34 mmol), triethylamine (0.09 mL, 0.64 mmol) and a catalytic amount of sodium iodide in anhydrous N,N-dimethylformamide (2.50 mL) was stirred at 110° C. overnight. The reaction mixture was concentrated in vacuo, taken-up in dichloromethane (5 mL) and washed with water (2×5 mL). The organic layer was dried ($Na_2SO_4$) and evaporated in vacuo. The crude product was passed through a SCX cartridge, washing with methanol and eluting with ammonia 2M in methanol and then purified by flash chromatography on silica gel, eluting with 2% methanol in dichloromethane, to afford the corresponding free base of the title compound as a yellow solid (65.9 mg, 52%).

The free base (58.4 mg, 0.14 mmol) was dissolved in dry dichloromethane (2 mL) and a 1.25 M solution of hydrochloric acid in methanol (0.30 mL, 0.37 mmol) was slowly added at 0° C. The resulting suspension was stirred at 0° C. for 2 h. Evaporation of the volatiles gave the title compound as a pale brown solid (42 mg). $^1$H NMR (500 MHz, DMSO-$d_6$) δ ppm 11.31-10.88 (m, 1H) 9.16-8.77 (m, 1H) 8.11-7.92 (m, 2H) 7.87 (d, 1H) 7.45 (d, 1H) 7.30 (dd, 1H) 6.80 (dd, 1H) 6.17 (t, 1H) 3.94 (t, 2H) 3.68 (s, 3H) 3.63-3.29 (m, 8H) 3.25-3.17 (m, 2H) 2.93 (s, 3H) 1.98-1.51 (m, 4H).

Biological Assays a) Human 5-$HT_{1A}$ Receptor Functional Potency

The functional potency of the compounds of the invention for the 5-$HT_{1A}$ receptor may be determined by the following GTPγS binding protocol. Cells used in the study are CHO Cells and Human Embryo Kidney (HEK293). Transfect cells with DNA coding for human receptor as follows: HEK293_5-$HT_{1A}$. Initially dissolve test compounds in 100% dimethyl sulfoxide to a concentration of 10 mM. Serially dilute the test compounds in 100% dimethyl sulphoxide using a Biomek FX in 384 well assay plates, so that the final top concentration of test compound is 3 μM in the assay. Add the test compound at 1.0% total assay volume (TAV) to a solid, white, 384 well assay plate (Griener). Add 50% TAV of precoupled (for 60 mins @ RT) membranes (6 ug/well), Wheatgerm Agglutinin Polystyrene Scintillation Proximity Assay beads (RPNQ0260 Amersham International) (0.25 mg/well) in 20 mM HEPES pH 7.4, 100 mM NaCl, 3 mM $MgCl_2$ and 10 μM GDP and saponin 60 m/well FAC was also added. The third addition may be either a 20% TAV addition of either; buffer for agonist format, or $EC_{80}$ final assay concentration (FAC) of agonist, prepared in assay buffer, 5HT, for antagonist format.

Start the assay by the addition of 29% TAV of GTPγS 0.38 nM FAC.

After all additions, incubate the assay plates at RT for 2-3 hours. Count the assay plates on a Viewlux, 613/55 filter for 5 mins. Read the assay plates between 3-6 hours after the final addition.

Using assay a) the compound of formula (I) gave an fpKi against $5-HT_{1A}$ of 9.3 b) Human $5-HT_{1A}$, $5-HT_{1B}$ and $5-HT_{1D}$ Receptor Affinity

The affinities of the compounds of the invention for the $5-HT_{1A}$, $5-HT_{1B}$ and $5-HT_{1D}$ receptors may be determined by the following assay.

Homogenise chinese hamster ovary (CHO) cells expressing $5-HT_{1A}$ receptors ($4 \times 10^7$ cells/ml) in Tris buffer and store in 1 ml aliquots. Homogenise CHO cells expressing $5-HT_{1B}$ receptors ($4 \times 10^7$ cells/ml) in Tris buffer and store in 1.5 ml aliquots. Homogenise CHO cells expressing $5-HT_{1D}$ receptors ($1 \times 10^8$/ml) in Tris buffer and stored in 1 ml aliquots. The binding assays are carried out in a total volume of 500 μl. For each compound to be tested make up seven solutions ranging in concentration from 0.3 mM to 0.3 nM (100× final concentrations). Dispense 5 μl of solution containing the test compound per well and add 100 μl of radioligand at 5× final desired assay concentration, i.e. [$^3$H]-5-HT 15 nM (final assay concentration: 3 nM) in Tris Mg HCl buffer (pH 7.7) for $5-HT_{1B/1D}$ receptors and [$^3$H]WAY100635 2.5 nM (final assay concentration: 0.5 nM) in Tris Mg HCl buffer (pH 7.7) containing 150 μM $GPP(NH)_p$ (final assay concentration: 30 μM) for $5-HT_{1A}$ receptors. Add 400 μl/well of a cell membrane suspension in Tris Mg HCl buffer (pH 7.7) to make a total volume of 505 μl. Incubate at 37° C. for 45 minutes. Determine non-specific binding using 0.01 mM 5-HT for $5-HT_{1B/1D}$ receptors and 0.01 mM WAY100635 for $5-HT_{1A}$ receptors. Terminate incubation by rapid filtration using a Packard Filtermate. Measure radioactivity using Topcount scintillation counting. Calculate pKi values from the $IC_{50}$ generated by an iterative least squares curve fitting programme.

Using assay b) the compound of formula (I) gave a pKi against $5-HT_{1A}$ of 9.3 and a pKi against $5-HT_{1B}$ of 6.7.

The invention claimed is:

1. A compound which is 3-(methyloxy)-1-{4-[4-(2-methyl-5-quinolinyl)-1-piperazinyl]butyl}-2(1H)-pyridinone of formula (I),

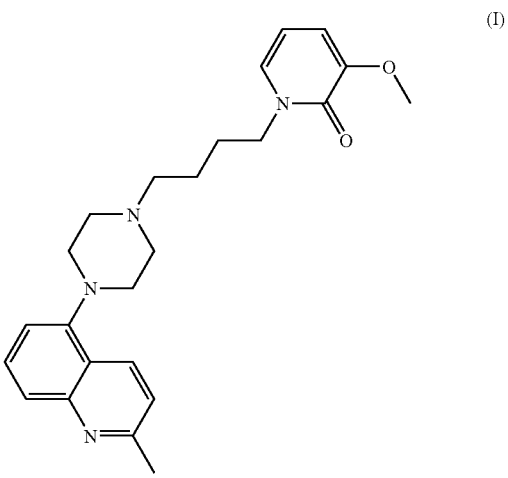

or a pharmaceutically acceptable salt thereof.

2. A method of treatment of premature ejaculation in a human in need thereof, which comprises administering to said human a therapeutically effective amount of the compound defined in claim 1, or a pharmaceutically acceptable salt thereof.

3. A pharmaceutical composition comprising the compound defined in claim 1, or a pharmaceutically acceptable salt thereof, and a pharmaceutically acceptable carrier or excipient.

4. A process for preparing a pharmaceutical composition comprising the compound defined in claim 1, or a pharmaceutically acceptable salt thereof, and a pharmaceutically acceptable carrier or excipient, the process comprising mixing the compound or salt, and the pharmaceutically acceptable carrier or excipient.

* * * * *